(12) United States Patent
Wei (10) Patent No.: US 10,130,465 B2
(45) Date of Patent: Nov. 20, 2018

(54) BIFURCATED TUBULAR GRAFT FOR TREATING TRICUSPID REGURGITATION

(71) Applicant: Abbott Cardiovascular Systems Inc., Santa Clara, CA (US)

(72) Inventor: Michael Francis Wei, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 15/051,045

(22) Filed: Feb. 23, 2016

(65) Prior Publication Data

US 2017/0239043 A1    Aug. 24, 2017

(51) Int. Cl.

| | |
|---|---|
| *A61F 2/06* | (2013.01) |
| *A61F 2/24* | (2006.01) |
| *A61F 2/07* | (2013.01) |
| *A61F 2/844* | (2013.01) |
| *A61F 2/90* | (2013.01) |

(52) U.S. Cl.
CPC .............. *A61F 2/2418* (2013.01); *A61F 2/07* (2013.01); *A61F 2/2412* (2013.01); *A61F 2/2433* (2013.01); *A61F 2/844* (2013.01); *A61F 2/90* (2013.01); *A61F 2002/065* (2013.01); *A61F 2230/006* (2013.01)

(58) Field of Classification Search
CPC ...... A61F 2/2418; A61F 2/2433; A61F 2/844; A61F 2/90; A61F 2002/065; A61F 2002/067; A61F 2/954; A61F 2/91; A61F 2/856; A61F 2/06; A61F 2/07; A61F 2230/006; A61F 2/24; A61F 2/2475
See application file for complete search history.

(56) References Cited

U.S. PATENT DOCUMENTS

| | | |
|---|---|---|
| 2,701,559 A | 2/1955 | Cooper |
| 2,845,959 A | 8/1958 | Sidebotham |
| 2,978,787 A | 4/1961 | Liebig |
| 2,990,605 A | 7/1961 | Demsyk |
| 3,029,819 A | 4/1962 | Starks |
| 3,096,560 A | 7/1963 | Liebig |
| 3,105,492 A | 10/1963 | Jeckel |
| 3,142,067 A | 7/1964 | Liebig |
| 3,657,744 A | 4/1972 | Ersek |
| 3,868,956 A | 3/1975 | Alfidi et al. |
| 3,908,662 A | 9/1975 | Razgulov et al. |

(Continued)

FOREIGN PATENT DOCUMENTS

| | | |
|---|---|---|
| EP | 461791 A1 | 1/1997 |
| FR | 2677872 A1 | 12/1992 |

(Continued)

OTHER PUBLICATIONS

International Search Report, dated Jun. 12, 2017, 4 pages, from PCT/US2017/018741 published as WO2017/147082 on Aug. 31, 2017.

*Primary Examiner* — Seema Mathew
(74) *Attorney, Agent, or Firm* — Fulwider Patton LLP (57) ABSTRACT

A lubricated tubular graft is implanted in the inferior vena cava and the superior vena cava in order to control the inflow of blood to the right atrium. A bifurcated leg with a non-collapsing stent extends across the tricuspid valve. A bioprosthetic valve is positioned proximal of the stent in the bifurcated leg in order to regulate flow through the tricuspid valve and to eliminate tricuspid regurgitation.

16 Claims, 9 Drawing Sheets

(56) References Cited

U.S. PATENT DOCUMENTS

| | | |
|---|---|---|
| 3,945,052 A | 3/1976 | Liebig |
| 3,993,078 A | 11/1976 | Bergentz et al. |
| 4,041,931 A | 8/1977 | Elliott et al. |
| 4,047,252 A | 9/1977 | Liebig et al. |
| 4,061,134 A | 12/1977 | Samuels et al. |
| 4,108,161 A | 8/1978 | Samuels et al. |
| 4,130,904 A | 12/1978 | Whalen |
| 4,140,126 A | 2/1979 | Choudhury |
| 4,159,719 A | 7/1979 | Haerr |
| 4,193,137 A | 3/1980 | Heck |
| 4,202,349 A | 5/1980 | Jones |
| 4,214,587 A | 7/1980 | Sakura |
| 4,323,071 A | 4/1982 | Simpson et al. |
| 4,387,952 A | 6/1983 | Slusher |
| 4,503,569 A | 3/1985 | Dotter et al. |
| 4,504,354 A | 3/1985 | George et al. |
| 4,512,338 A | 4/1985 | Balko et al. |
| 4,516,972 A | 5/1985 | Samson |
| 4,517,687 A | 5/1985 | Liebig et al. |
| 4,531,933 A | 7/1985 | Norton et al. |
| 4,553,545 A | 11/1985 | Maass et al. |
| 4,560,374 A | 12/1985 | Hammerslag |
| 4,562,596 A | 1/1986 | Kornberg |
| 4,577,631 A | 3/1986 | Kreamer |
| 4,580,568 A | 4/1986 | Gianturco |
| 4,616,652 A | 10/1986 | Simpson et al. |
| 4,617,932 A | 10/1986 | Kornberg |
| 4,619,246 A | 10/1986 | Molgaard et al. |
| 4,649,922 A | 3/1987 | Wiktor |
| 4,650,466 A | 3/1987 | Luther |
| 4,652,263 A | 3/1987 | Herweck et al. |
| 4,655,771 A | 4/1987 | Wallsten |
| 4,665,918 A | 5/1987 | Garza et al. |
| 4,681,110 A | 7/1987 | Wiktor |
| 4,693,249 A | 9/1987 | Schenck et al. |
| 4,706,671 A | 11/1987 | Weinrib et al. |
| 4,728,328 A | 3/1988 | Hughes et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,774,949 A | 10/1988 | Fogarty et al. |
| 4,776,337 A | 10/1988 | Palmaz |
| 4,787,899 A | 11/1988 | Lazarus |
| 4,793,348 A | 12/1988 | Palmaz |
| 4,795,458 A | 1/1989 | Regan et al. |
| 4,795,465 A | 1/1989 | Marten |
| 4,800,882 A | 1/1989 | Gianturco et al. |
| 4,817,624 A | 4/1989 | Newbower et al. |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor et al. |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco et al. |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | Dipisa, Jr. |
| 4,943,346 A | 7/1990 | Mattelin et al. |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,969,896 A | 11/1990 | Shors |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco et al. |
| 5,047,050 A | 9/1991 | Arpesani |
| 5,059,211 A | 10/1991 | Stack et al. |
| 5,061,273 A | 10/1991 | Yock et al. |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada et al. |
| 5,089,006 A | 2/1992 | Stiles |
| 5,092,877 A | 3/1992 | Pinchuk |
| 5,098,374 A | 3/1992 | Othel et al. |
| 5,100,429 A | 3/1992 | Sinofsky et al. |
| 5,102,417 A | 4/1992 | Palmaz |
| 5,104,399 A | 4/1992 | Lazarus |
| 5,104,404 A | 4/1992 | Wolff |
| 5,108,416 A | 4/1992 | Ryan et al. |
| 5,108,417 A | 4/1992 | Sawyer et al. |
| 5,108,424 A | 4/1992 | Hoffman, Jr. et al. |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,135,536 A | 8/1992 | Hillstead |
| 5,147,385 A | 9/1992 | Beck et al. |
| 5,156,619 A | 10/1992 | Ehrenfeld |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,178,630 A | 1/1993 | Schmitt |
| 5,178,634 A | 1/1993 | Ramos Martinez |
| 5,180,368 A | 1/1993 | Garrison et al. |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,976 A | 3/1993 | Herweck et al. |
| 5,197,977 A | 3/1993 | Hoffman, Jr. et al. |
| 5,197,978 A | 3/1993 | Hess |
| 5,201,901 A | 4/1993 | Harada et al. |
| 5,217,482 A | 6/1993 | Keith |
| 5,222,971 A | 6/1993 | Willard et al. |
| 5,226,913 A | 7/1993 | Pinchuk |
| 5,234,416 A | 8/1993 | MacAulay et al. |
| 5,234,456 A | 8/1993 | Silvestrini et al. |
| 5,242,394 A | 9/1993 | Tremulis |
| 5,242,399 A | 9/1993 | Lau et al. |
| 5,242,452 A | 9/1993 | Inoue |
| 5,275,622 A | 1/1994 | Lazarus et al. |
| 5,282,823 A | 2/1994 | Schwartz et al. |

(56) References Cited

U.S. PATENT DOCUMENTS

| | | |
|---|---|---|
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,298,115 A | 3/1994 | Leonard |
| 5,304,200 A | 4/1994 | Spaulding |
| 5,304,220 A | 4/1994 | Maginot |
| 5,314,444 A | 5/1994 | Gianturco et al. |
| 5,314,472 A | 5/1994 | Fontaine et al. |
| 5,316,023 A | 5/1994 | Palmaz et al. |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland et al. |
| 5,360,443 A | 11/1994 | Barone et al. |
| 5,368,566 A | 11/1994 | Crocker et al. |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,421,955 A | 6/1995 | Lau et al. |
| 5,423,745 A | 6/1995 | Todd et al. |
| 5,423,885 A | 6/1995 | Williams |
| 5,443,497 A | 8/1995 | Venbrux |
| 5,443,498 A | 8/1995 | Fontaine |
| 5,445,646 A | 8/1995 | Euteneuer et al. |
| 5,449,373 A | 9/1995 | Pinchasik et al. |
| 5,456,694 A | 10/1995 | Marin et al. |
| 5,456,712 A | 10/1995 | Maginot |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,197,978 B1 | 5/1996 | Hess |
| 5,514,154 A | 5/1996 | Lau et al. |
| 5,522,880 A | 6/1996 | Barone et al. |
| 5,527,355 A | 6/1996 | Ahn |
| 5,545,132 A | 8/1996 | Fagan et al. |
| 5,562,724 A | 10/1996 | Vorwerk et al. |
| 5,562,726 A | 10/1996 | Chuter |
| D376,011 S | 11/1996 | Nunokawa |
| 5,571,135 A | 11/1996 | Fraser et al. |
| 5,571,170 A | 11/1996 | Palmaz et al. |
| 5,571,171 A | 11/1996 | Barone et al. |
| 5,571,173 A | 11/1996 | Parodi |
| 5,575,817 A | 11/1996 | Martin |
| 5,578,072 A | 11/1996 | Barone et al. |
| 5,591,228 A | 1/1997 | Edoga |
| 5,591,229 A | 1/1997 | Parodi |
| 5,603,721 A | 2/1997 | Lau et al. |
| 5,609,627 A | 3/1997 | Goicoechea et al. |
| 5,613,980 A | 3/1997 | Chauhan |
| 5,617,878 A | 4/1997 | Taheri |
| 5,626,604 A | 5/1997 | Cottone |
| 5,632,763 A | 5/1997 | Glastra |
| 5,639,278 A | 6/1997 | Dereume et al. |
| 5,643,340 A | 7/1997 | Nunokawa |
| 5,653,690 A | 8/1997 | Booth et al. |
| 5,653,691 A | 8/1997 | Rupp et al. |
| 5,653,727 A | 8/1997 | Wiktor |
| 5,669,924 A | 9/1997 | Shaknovich |
| 5,676,696 A | 10/1997 | Marcade |
| 5,676,697 A | 10/1997 | McDonald |
| 5,683,450 A | 11/1997 | Goicoechea et al. |
| 5,683,452 A | 11/1997 | Barone et al. |
| 5,683,453 A | 11/1997 | Palmaz |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,709,713 A | 1/1998 | Evans et al. |
| 5,713,363 A | 2/1998 | Seward et al. |
| 5,713,917 A | 2/1998 | Leonhardt et al. |
| 5,716,396 A | 2/1998 | Williams, Jr. |
| 5,720,726 A | 2/1998 | Marcadis et al. |
| 5,720,735 A | 2/1998 | Dorros |
| 5,720,776 A | 2/1998 | Chuter et al. |
| 5,733,303 A | 3/1998 | Israel et al. |
| 5,733,325 A | 3/1998 | Robinson et al. |
| 5,735,893 A | 4/1998 | Lau et al. |
| 5,749,825 A | 5/1998 | Fischell et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,776,180 A | 7/1998 | Goicoechea et al. |
| 5,782,855 A | 7/1998 | Lau et al. |
| 5,782,906 A | 7/1998 | Marshall et al. |
| 5,786,339 A | 7/1998 | Agouridas et al. |
| 5,800,508 A | 9/1998 | Goicoechea et al. |
| 5,800,520 A | 9/1998 | Fogarty et al. |
| 5,800,521 A | 9/1998 | Orth |
| 5,810,871 A | 9/1998 | Tuckey et al. |
| 5,817,152 A | 10/1998 | Birdsall et al. |
| 5,830,217 A | 11/1998 | Ryan et al. |
| 5,836,965 A | 11/1998 | Jendersee et al. |
| 5,893,852 A | 4/1999 | Morales |
| 5,893,887 A | 4/1999 | Jayaraman |
| 5,895,407 A | 4/1999 | Jayaraman |
| 5,902,332 A | 5/1999 | Schatz |
| 5,906,640 A | 5/1999 | Penn et al. |
| 5,913,895 A | 6/1999 | Burpee et al. |
| 5,916,234 A | 6/1999 | Lam |
| 5,984,964 A | 11/1999 | Roberts et al. |
| 5,997,468 A | 12/1999 | Wolff et al. |
| 6,030,413 A | 2/2000 | Lazarus |
| 6,056,775 A | 5/2000 | Borghi et al. |
| 6,066,168 A | 5/2000 | Lau et al. |
| 6,086,604 A | 7/2000 | Fischell et al. |
| 6,096,073 A | 8/2000 | Webster et al. |
| 6,146,358 A | 11/2000 | Rowe |
| 6,165,195 A | 12/2000 | Wilson et al. |
| 6,179,868 B1 | 1/2001 | Burpee et al. |
| 6,183,506 B1 | 2/2001 | Penn et al. |
| 6,183,509 B1 | 2/2001 | Dibie |
| 6,190,403 B1 | 2/2001 | Fischell et al. |
| 6,217,608 B1 | 4/2001 | Penn et al. |
| 6,264,686 B1 | 7/2001 | Rieu et al. |
| 6,371,961 B1 | 4/2002 | Osborne et al. |
| 6,503,272 B2 | 1/2003 | Duerig et al. |
| 6,669,722 B2 | 12/2003 | Chen et al. |
| 6,699,278 B2 | 3/2004 | Fischell et al. |
| 6,749,628 B1 | 6/2004 | Callol et al. |
| 6,780,174 B2 | 8/2004 | Mauch |
| 6,962,602 B2 | 11/2005 | Vardi et al. |
| 7,241,257 B1 | 7/2007 | Ainsworth et al. |
| 7,250,041 B2 | 7/2007 | Chiu et al. |
| 7,799,072 B2 | 9/2010 | Greenberg |
| 7,955,379 B2 | 6/2011 | Wilson et al. |
| 8,029,558 B2 | 10/2011 | Ta et al. |
| 8,226,710 B2 | 7/2012 | Nguyen et al. |
| 8,252,051 B2 | 8/2012 | Chau et al. |
| 8,870,944 B2 | 10/2014 | Sochman et al. |
| 8,940,040 B2 * | 1/2015 | Shahriari ............... A61F 2/07 623/1.12 |
| 9,023,098 B2 | 5/2015 | Kuehn |
| 2002/0077692 A1 * | 6/2002 | Besselink ............... A61F 2/86 623/1.12 |
| 2003/0033005 A1 * | 2/2003 | Houser ............... A61B 17/11 623/1.35 |
| 2003/0139805 A1 * | 7/2003 | Holmberg ............... A61F 2/06 623/1.31 |
| 2003/0204243 A1 * | 10/2003 | Shiu ............... A61F 2/07 623/1.16 |
| 2004/0199238 A1 * | 10/2004 | Brown ............... A61B 5/0031 623/1.1 |
| 2004/0260389 A1 * | 12/2004 | Case ............... A61F 2/2418 623/1.24 |
| 2007/0050015 A1 * | 3/2007 | O'Brien ............... A61F 2/07 623/1.35 |

(56) References Cited

U.S. PATENT DOCUMENTS

| | | | |
|---|---|---|---|
| 2007/0213813 A1* | 9/2007 | Von Segesser | A61F 2/2418 623/2.18 |
| 2011/0301700 A1* | 12/2011 | Fish | A61F 2/0095 623/2.11 |
| 2012/0123527 A1* | 5/2012 | Isch | A61L 31/06 623/1.35 |
| 2012/0136430 A1* | 5/2012 | Sochman | A61F 2/2418 623/1.23 |
| 2013/0158673 A1* | 6/2013 | Toomey | A61F 2/04 623/23.7 |
| 2014/0142691 A1 | 5/2014 | Pouletty | |
| 2014/0277348 A1* | 9/2014 | Roeder | A61F 2/07 623/1.11 |
| 2015/0223793 A1 | 8/2015 | Goldfarb et al. | |
| 2015/0282958 A1* | 10/2015 | Centola | A61F 2/852 623/2.15 |

FOREIGN PATENT DOCUMENTS

| | | |
|---|---|---|
| JP | 62213762 A | 9/1987 |
| JP | 62235496 A | 10/1987 |
| JP | 63246178 A | 10/1988 |
| JP | 01083685 A | 3/1989 |
| JP | 03009745 A | 1/1991 |
| JP | 03009746 A | 1/1991 |
| SU | 1217402 A1 | 3/1986 |
| SU | 1318235 A1 | 6/1987 |
| SU | 1389778 A2 | 4/1988 |
| SU | 1457921 A1 | 2/1989 |
| SU | 1482714 A2 | 5/1989 |
| WO | 9624306 A1 | 8/1996 |
| WO | 9716217 A1 | 5/1997 |
| WO | 9836709 A1 | 8/1998 |

* cited by examiner

BIFURCATED TUBULAR GRAFT FOR TREATING TRICUSPID REGURGITATION

BACKGROUND

The human heart includes four chambers, which are the left and right atrium and the left and right ventricles. The mitral valve, which allows blood flow in one direction, is positioned between the left ventricle and left atrium. The tricuspid valve is positioned between the right ventricle and the right atrium. The aortic valve is positioned between the left ventricle and the aorta, and the pulmonary valve is positioned between the right ventricle and pulmonary artery. The heart valves function in concert to move blood throughout the circulatory system.

If the valves of the heart do not function properly, due either to disease or congenital defects, the circulation of the blood may be compromised. Diseased heart valves may be stenotic, wherein the valve does not open sufficiently to allow adequate forward flow of blood through the valve, and/or incompetent, wherein the valve does not close completely. Incompetent heart valves cause regurgitation or excessive backward flow of blood through the valve when the valve is closed. For example, certain diseases of the heart valves can result in dilation of the heart and one or more heart valves. When a heart valve annulus dilates, the valve leaflet geometry deforms and causes ineffective closure of the valve leaflets. The ineffective closure of the valve can cause regurgitation of the blood, accumulation of blood in the heart, and other problems. Valvular regurgitation can occur when the valve leaflets (for the tricuspid and mitral valve) or the valve cusps (for the aortic or pulmonary valve) do not coapt properly when the valve is closed. This can be caused by a variety of disease processes, including, e.g., leaflet or cusp retraction, annular dilatation (e.g., annuloaortic ectasia, mitral or tricuspid annular dilatation, etc.), etc. Also, the leaflets or cusps of a valve can prolapse (or fall back) as a result of stretching or rupture of their support system. What all these processes have in common is that an orifice (a regurgitant orifice) remains after valve closure through which blood can flow backwards (i.e., not in the intended direction), thus creating valve regurgitation.

Diseased or damaged heart valves can be treated by valve replacement surgery, in which damaged leaflets are excised and the annulus is sculpted to receive a replacement valve. Another repair technique that has been shown to be effective in treating incompetence is annuloplasty, in which the effective size of the valve annulus is contracted by attaching a prosthetic annuloplasty repair segment or ring to an interior wall of the heart around the valve annulus. The annuloplasty ring reinforces the functional changes that occur during the cardiac cycle to improve coaptation and valve integrity. Thus, annuloplasty rings help reduce reverse flow or regurgitation while permitting good hemodynamics during forward flow.

Annuloplasty rings may be stiff or flexible, may be open or closed, and may have a variety of shapes including circular, D-shaped, or C-shaped. The configuration of the ring is generally based on the shape of the heart valve being repaired or on the particular application. For example, the tricuspid valve is generally circular and the mitral valve is generally D-shaped. Further, C-shaped rings may be used for tricuspid valve repairs, for example, because it allows a surgeon to position the break in the ring adjacent the atrioventricular (AV) node, thus avoiding the need for suturing at that location. All of these prior art procedures are complicated repairs that involve risks to the patient. The present invention improves blood flow through the tricuspid valve and prevents regurgitation and is delivered and implanted minimally invasively thereby reducing risks and improving patient safety.

SUMMARY OF THE INVENTION

A device and method of use is provided for reducing cardiac valve regurgitation, and more particularly, provides a device designed to regulate flow through the tricuspid valve and reduce the likelihood or prevent regurgitation through the tricuspid valve.

In one embodiment, a tubular graft having a Y-shaped configuration includes a tubular main body and a tubular leg portion extending from the tubular main body and being in fluid communication with the tubular main body. The tubular main body has a first end extending into the superior vena cava (SVC) and a first stent adjacent the first end of the tubular main body for attaching the tubular main body to the SVC. The tubular main body has a second end extending into the inferior vena cava (IVC) and a second stent adjacent the second end for attaching the tubular main body to the IVC. The tubular leg portion extends from the tubular main body and is in fluid communication with the tubular main body. The tubular leg portion is configured for extending into and through the right atrium and through the tricuspid valve. The tubular leg portion has a third stent adjacent a distal end of the tubular leg portion to hold open the tricuspid valve. A bioprosthetic valve is positioned in the tubular leg portion and spaced proximal to the third stent a distance in the range from 0.0394 in. to 1.1811 in. (1.0 mm to 30.0 mm). In one embodiment, the bioprosthetic valve is positioned in the tubular portion and spaced proximal to the third stent a distance in the range from 0.1969 in. to 0.7874 in. (5.0 mm to 20.0 mm). In another embodiment, the bioprosthetic valve is positioned in the tubular leg portion and spaced proximal to the third stent a distance in the range from 0.0394 in. to 0.3937 in. (1.0 mm to 10.0 mm). In yet another embodiment, the bioprosthetic valve is positioned in the tubular leg portion and abuts the third stent.

In another embodiment, a bifurcated endograft has a Y-shaped configuration and includes a first leg, a second leg, and a third leg, all in fluid communication with each other. The first leg has a first length and is configured for extending into the SVC and a first stent adjacent a distal end of the first leg for attaching the first leg to the SVC. The second leg has a second length and is configured for extending into the IVC and a second stent adjacent the distal end of the second leg for attaching the second leg to the IVC. A third leg has a third length and is configured for extending into the right atrium and through the tricuspid valve. The third leg has a third stent adjacent a distal end of the third leg to hold open the tricuspid valve. A bioprosthetic valve is positioned in the third leg and spaced proximal to the third stent a distance in the range from 0.0394 in. to 1.1811 in. (1.0 mm to 30.0 mm). In another embodiment, the bioprosthetic valve is positioned in the third leg and spaced proximal to the third stent a distance in the range from 0.1969 in. to 0.7874 in. (5.0 mm to 20.0 mm). In another embodiment, the bioprosthetic valve is positioned in the third leg and spaced proximal to the third stent a distance in the range from 0.0394 in. to 0.3937 in. (1.0 mm to 10.0 mm). In yet another embodiment, the bioprosthetic valve is positioned in the third leg and abuts the third stent.

DETAILED DESCRIPTION OF THE PREFERRED EMBODIMENTS

Figure 1:
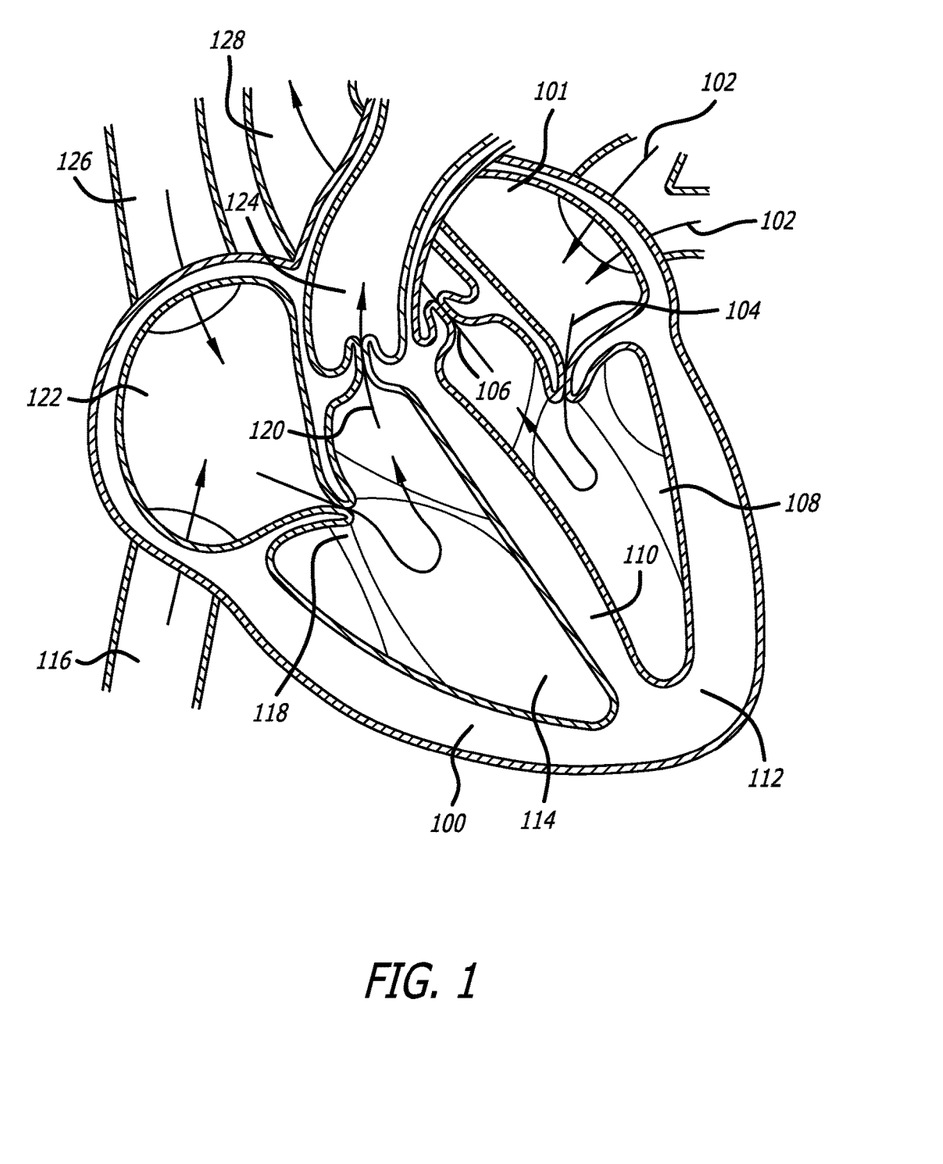
FIG. 1 schematically illustrates a cross-section of the heart showing blood flow throughout the heart.

Referring to FIG. 1, a cross-sectional view of a heart is shown to illustrate blood flow throughout the heart. Deoxygenated blood returning from the body comes into heart 100 from either superior vena cava 126 or inferior vena cava 116 and collects in right atrium 122. Right atrium 122 contracts to pump the blood through tricuspid valve 118 where it flows into right ventricle 114. Right ventricle 114 contracts to send the blood through pulmonary valve 120 into pulmonary artery 124 where it goes into the lungs (not shown). The oxygenated blood returning from the lungs flows through pulmonary veins 102 where it flows into left atrium 101. Left atrium 101 contracts sending the blood through bicuspid or mitral valve 104 and into left ventricle 108. When left ventricle 108 contracts, the blood is sent through aortic valve 106 and into aorta 128. Left ventricle 108 and right ventricle 114 are separated by ventricular septum 110.

If there is a problem with aortic valve 106, when left ventricle 108 expands to take in blood through mitral valve 104 from left atrium 101, left ventricle 108 may also suck blood back into the left ventricle 108 from the aorta 128 through the aortic valve 106. This back flow of blood from aorta 128 into left ventricle 108 can occur if the aortic valve 106 is not properly functioning. In order to repair a non-functioning aortic valve 106, a patient's heart is normally arrested and the patient is placed on cardiopulmonary bypass so that a surgery on the aortic valve 106 can be performed. It is difficult to perform a percutaneous aortic valve 106 repair or replacement while the heart is beating, since blood needs to flow through the heart 100 by flowing into pulmonary veins 102 into left atrium 101, through mitral valve 104 into left ventricle 108 across aortic valve 106 and into aorta 128 to be fed to the rest of the body. If there are a number of tools (not shown) that are blocking the aorta 128 that are being used to operate on aortic valve 106, then this blood flow cannot occur normally. In order to perform a surgery on aortic valve 106 without cardiopulmonary bypass, normal blood flow needs to occur through heart 100 and the rest of the body.

Similar problems of heart surgeries or procedures are encountered when working on mitral valve 104, tricuspid valve 118, pulmonary valve 120, and ventricular septum 110. In order to conduct a successful procedure on an area of heart 100, it is necessary to place an inlet of a pump upstream of the area and an outlet of a pump downstream of the area that is going to be worked on, when the area that will be worked on will be blocked by the tools that are used to perform the procedure.

Figure 2:
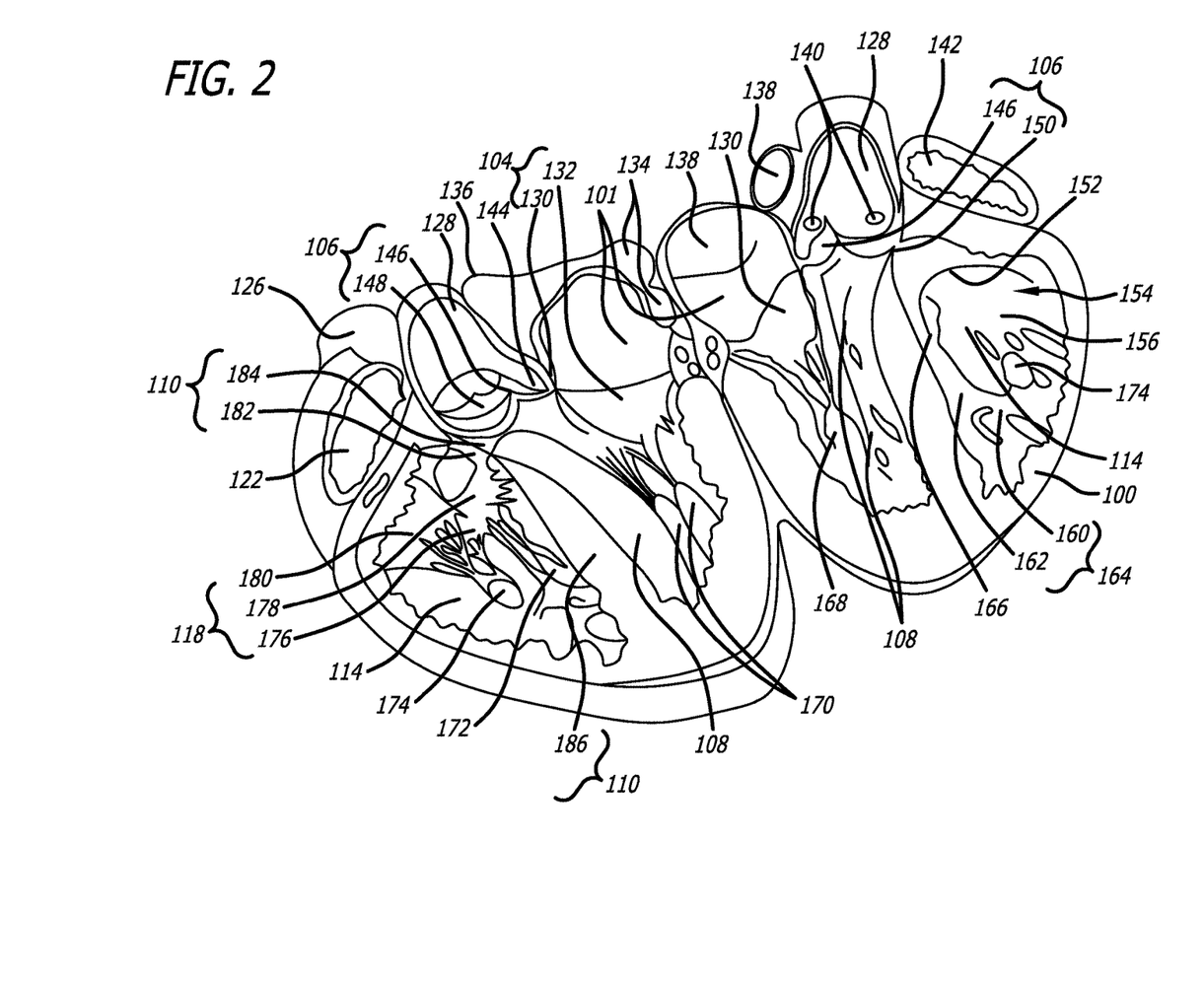
FIG. 2 schematically illustrates a vertical cross-section of the heart.

Referring to FIG. 2, a more detailed vertical cross-section of heart 100 is shown. Blood first collects in right atrium 122 from superior vena cava 126 or other veins. Right atrium 122 also includes right auricle 142. When right atrium 122 contracts, blood is sent through tricuspid valve 118 and into right ventricle 114. Tricuspid valve 118 is made up of three cusps: posterior cusp 176, septal cusp 178, and anterior cusp 180 (shown retracted). Right ventricle 114 has a number of muscles that contract to send blood out of right ventricle 114. Some of the muscles in right ventricle 114 include right anterior papillary muscle 174 (shown cut), and right posterior papillary muscle 172. Other parts of the anatomy of right ventricle 114 includes conus arteriosis 156, supra ventricular crest 152, and moderator band 160 and septal band 162 of septal marginal trabacula 164. The blood outflow to the pulmonary trunk is marked by arrow 154. Pulmonary trunk is shown as 138. The blood returning from the lungs returns by left pulmonary veins 134 and right pulmonary veins 136 where it collects in left atrium 101. Left atrium 101 also includes left auricle 138. When left atrium 101 contracts, blood is sent through mitral valve 104 which is made up of posterior cusp 132 and anterior cusp 130. Blood flows through mitral valve 104 and into left ventricle 108. Muscles in the left ventricle include left posterior papillary muscle 170, left anterior papillary muscle 168. Septum 110 separates left ventricle 108 from right ventricle 114. Septum 110 includes the muscular part of intraventricular septum 186, interventricular part of the membranous septum 182, and the atrial ventricular part of membranous septum 184. When left ventrical 108 contracts, blood is sent through aortic valve 106 which includes left semi-lunar cusp 146, posterior semi-lunar (non-coronary) cusp 148, and right semi-lunar cusp 150. Most of the blood flows through aortic valve 106 and into ascending aorta 128, although some of the blood is diverted into the openings of coronary arteries 140.

Figure 3:
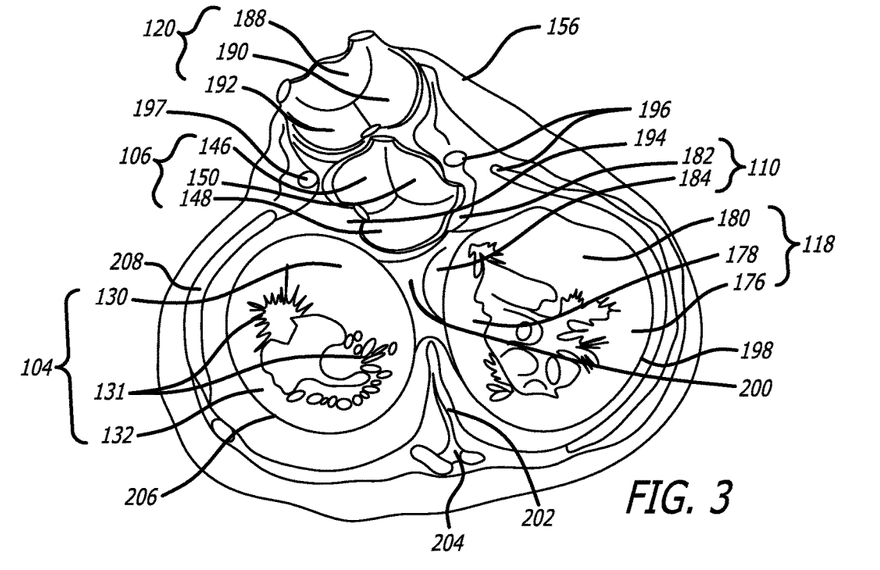
FIG. 3 schematically illustrates a horizontal cross-section of the heart in diastole showing valve operation.

Referring now to FIG. 3, is a horizontal cross-section of the heart showing the heart in diastole viewed from the base with the atria removed. Pulmonary valve 120 is shown in a closed position. Pulmonary valve 120 includes anterior semi-lunar cusp 198, right semi-lunar cusp 190, and left semi-lunar cusp 192. Aortic valve 106 is also shown in a closed position. Aortic valve 106 includes right (coronary) semi-lunar cusp 150, left (coronary) semi-lunar cusp 146, and posterior (non-coronary) semi-lunar cusp 148. The circumflex branch of the left coronary artery is labeled as reference number 208. Mitral valve 104 (between left atrium 101 and left ventricle 108) is shown in an open position. Mitral valve 104 includes anterior cusp 130, posterior cusp 132, and commissural cusps 131. There is also left fibrous ring 206 of mitral valve 104.

At the base of FIG. 3 (as viewed) is the posterior intraventricular branch of right coronary artery 204 and the atrial ventricular nodal branch of right coronary artery 202. In the middle of the heart is right fibrous trigone 200.

Tricuspid valve 118 between the right atrium 122 and the right ventricle 114 is shown in an open position and includes anterior cusp 180, septal cusp 178, and posterior cusp 176. Surrounding tricuspid valve 118 is a right fibrous ring of tricuspid valve 198. Membranous septum 110 includes intra-ventricular part 182 (shown by a broken line) and atrial-ventricular part 184. Right coronary artery is shown as 196, and left coronary artery is shown as 197. Left fibrous trigone is shown as 194, and conus arteriosis is shown as 156.

Figure 4:
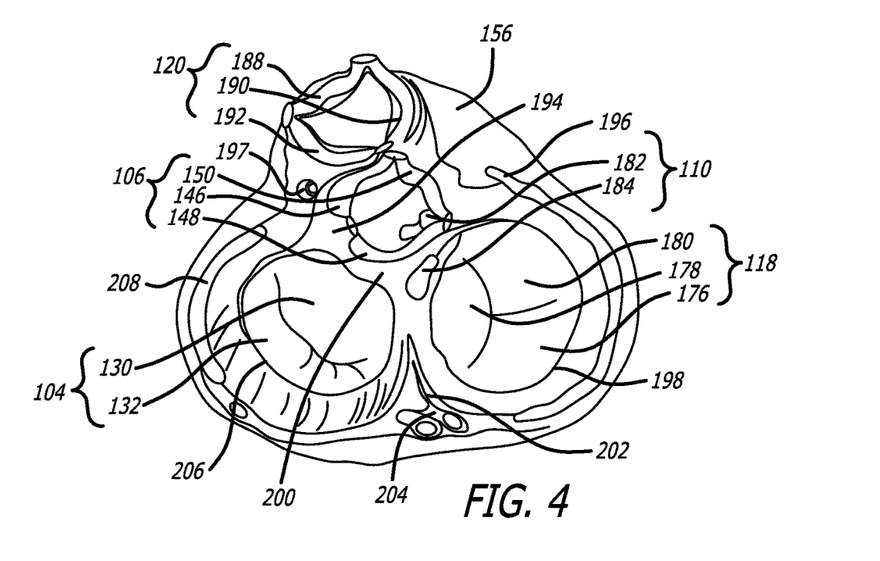
FIG. 4 schematically illustrates a horizontal cross-section of the heart in systole showing valve operation.
Figure 5:
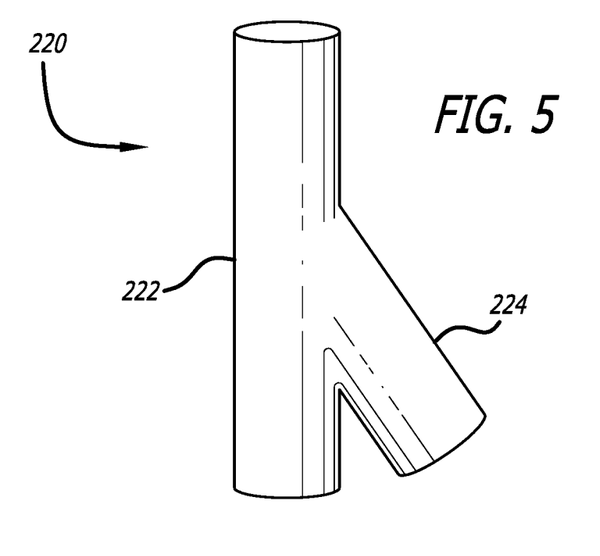
FIG. 5 is a plan view of the tubular graft.
Figure 6:
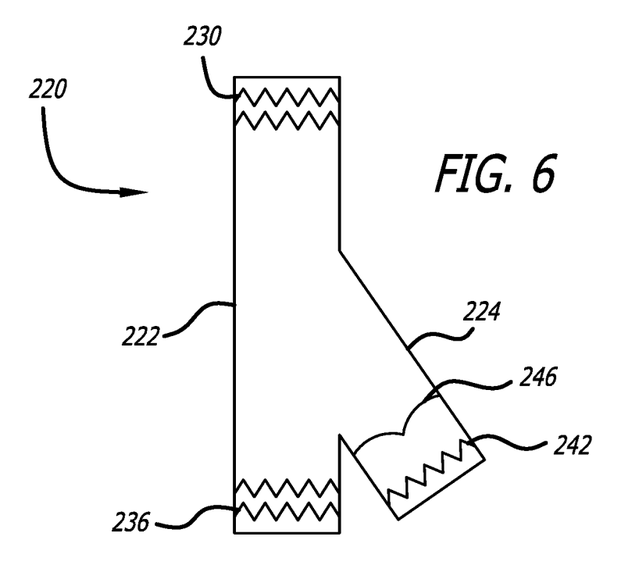
FIG. 6 is a plan view, in cross-section, showing the tubular graft, the stents for attaching the graft to the vessel walls, and a prosthetic valve.
Figure 7:
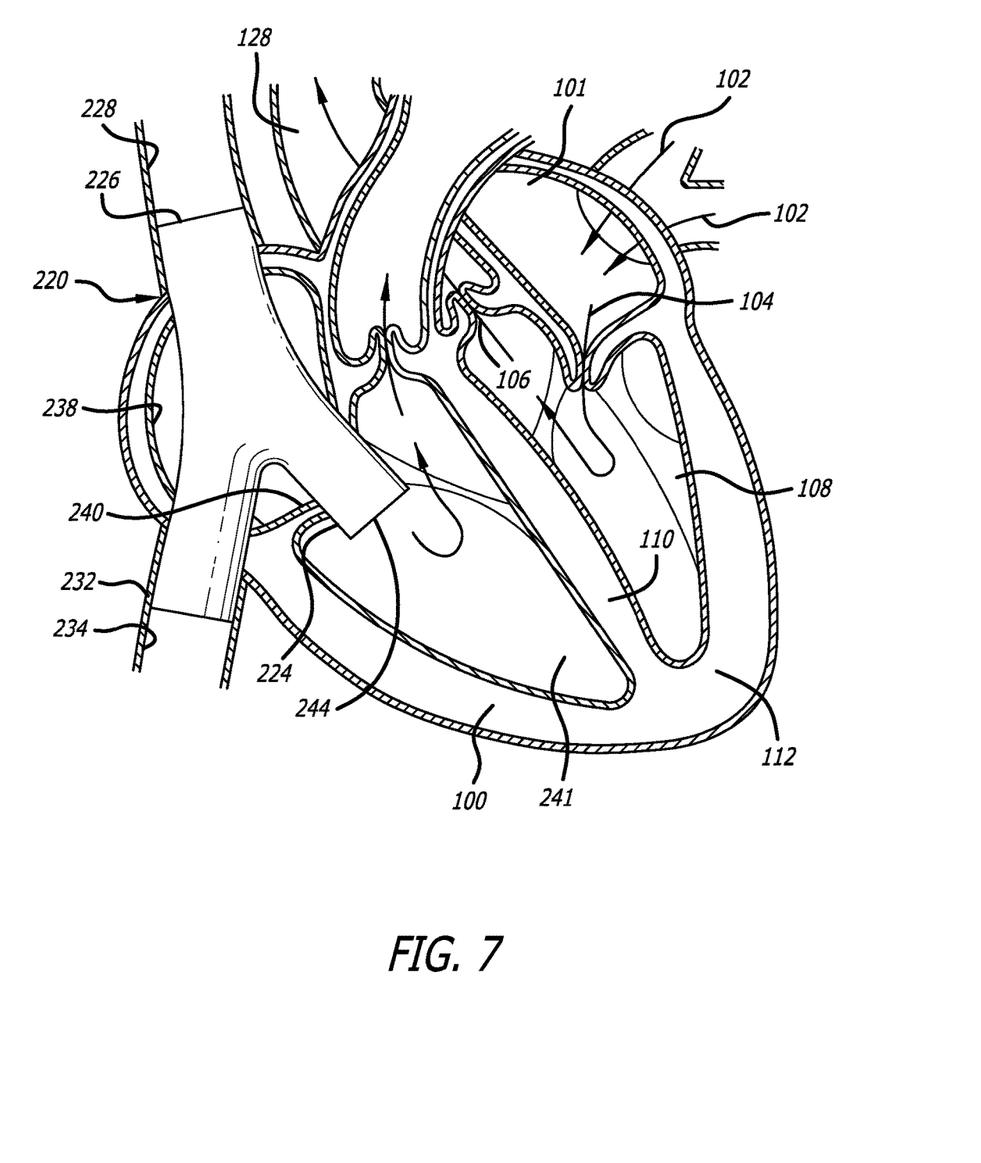
FIG. 7 schematically illustrates the tubular graft implanted in the SVC, IVC, and extending across the tricuspid valve.
Figure 8:
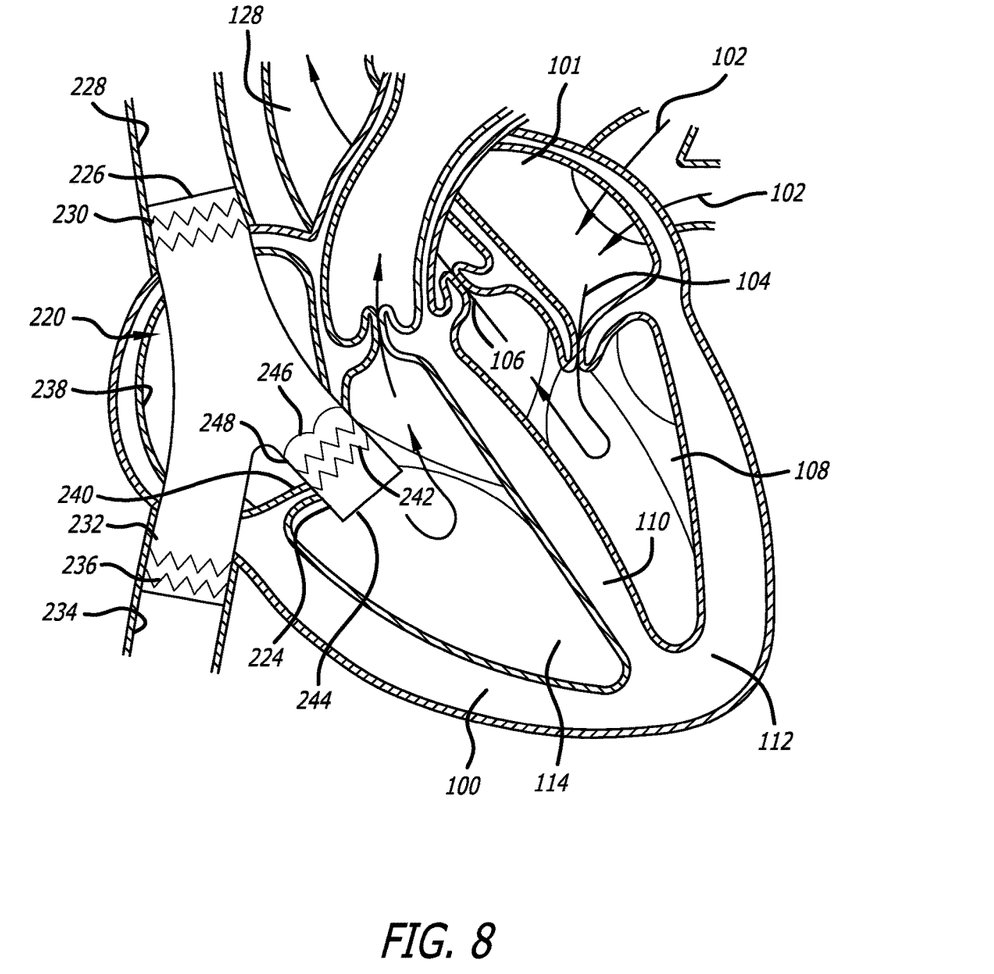
FIG. 8 is a schematic view of the tubular graft in cross-section, implanted in the SVC, IVC, and across the tricuspid valve.

Referring to FIG. 4 is the heart in systole viewed from the base with the atria removed. All of the parts are essentially the same as in FIG. 3, however, in this figure, aortic valve 106 and pulmonary valve 120 are shown open and tricuspid valve 118 and mitral valve 104 are shown closed. Again, pulmonary valve 120 has anterior semi-lunar cusp 188, right semi-lunar cusp 190, and left semi-lunar cusp 192. Aortic valve 106 is made up of right (coronary) semi-lunar cusp 150, left (coronary) semi-lunar cusp 146, and posterior (non-coronary) semi-lunar cusp 148. Mitral valve 104 is shown with anterior cusp 130 and posterior cusp 132 surrounded by left fibrous ring 206. Tricuspid valve 118 is shown with anterior cusp 180, septal cusp 178, posterior cusp 176, surrounded by right fibrous ring of tricuspid valve 198. Right coronary artery is shown as 196 with atrial ventricular branch 202 of right coronary artery 196 and posterior interventricular branch 204 of right coronary artery 196 showing. Left coronary artery 197 is also shown. Other parts of the heart shown in B are the same as those shown in A.

The oxygenated blood of the body originates in heart 100 and is pumped by the left ventricle (not shown) into aorta 128. From aorta 128, some blood is supplied to heart 100 through right coronary artery 196 and left coronary artery 197, the remaining blood branches throughout the rest of the body. A first branch, subclavian artery feeds axillary artery which turns into brachial artery to feed blood to the arms. Brachial artery in turn feeds radial artery and ulnar artery. Another branch off of aorta 128 is common carotid artery which feeds blood to the head. Superior mesenteric artery and inferior mesenteric artery feed blood to the abdomen. There is a common iliac artery for both legs. The common iliac artery in turn branches into external iliac artery and femoral artery. One of the branches of femoral artery is popliteal artery which branches into anterior tibial artery, posterior tibial artery, and dorsalis pedis artery. Peroneal artery branches off of external iliac artery.

The deoxygenated blood returns to heart 100 through the venous system. Some blood returning from the legs flows into posterior tibial vein, and anterior tibial vein, which feed into popliteal vein, and flows into femoral vein. Another vein in the legs is great saphenous vein which also feeds into femoral vein. Blood then flows into either internal iliac vein or external iliac vein which then flow into common iliac vein to return to heart 100 via inferior vena cava 284. Other branches feeding into inferior vena cava 284 include hepatic vein. Blood returning from the arms flows into ulnar vein, radial vein, brachial vein, or basilic vein, and flows into axillary vein. Blood flows from axillary vein into left or right innominate vein which flows into superior vena cava. Blood also flows into superior vena cava 278 from right subclavian vein, and from external jugular vein and internal jugular vein.

A device and method of use is provided for reducing cardiac valve regurgitation, and more particularly, the device is designed to regulate flow through the tricuspid valve and reduce the likelihood or prevent regurgitation through the tricuspid valve.

Figure 9:
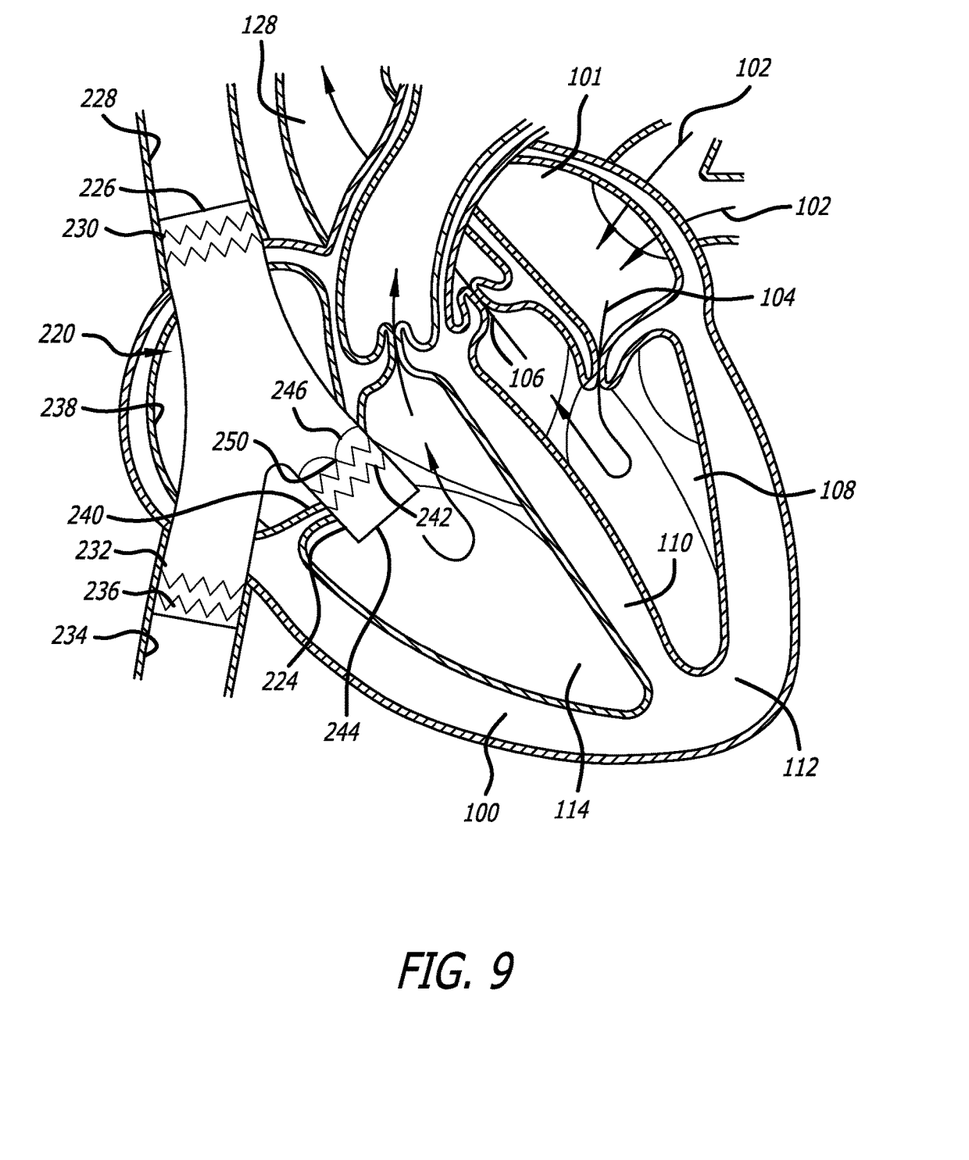
FIG. 9 schematically illustrates the tubular graft in cross-section and implanted in the SVC, IVC, and across the tricuspid valve, with the prosthetic valve abutting the third stent.

In one embodiment shown in FIGS. 5-9, a tubular graft 220 having a Y-shaped configuration includes a tubular main body 222 and a tubular leg portion 224 extending from the tubular main body and being in fluid communication with the tubular main body. The tubular main body 222 has a first end 226 extending into the superior vena cava (SVC) 228, and a first stent 230 adjacent the first end of the tubular main body for attaching the tubular main body to the SVC. The tubular main body 222 has a second end 232 extending into the inferior vena cava (IVC) 234 and a second stent 236 adjacent the second end for attaching the tubular main body to the IVC. The tubular leg portion 224 extends from the tubular main body 222 and is in fluid communication with the tubular main body. The tubular leg portion 224 is configured for extending into and through the right atrium 238 and through the tricuspid valve 240. The tubular leg portion has a third stent 242 adjacent a distal end 244 of the tubular leg portion to hold open the tricuspid valve. A bioprosthetic valve 246 is positioned in the tubular leg portion 224 and spaced proximal to the third stent 242 a distance 248 in the range from 0.0394 in. to 1.1811 in. (1.0 mm to 30.0 mm). In one embodiment, the bioprosthetic valve is positioned in the tubular leg portion and spaced proximal to the third stent a distance in the range from 0.1969 in. to 0.7874 in. (5.0 mm to 20.0 mm). In another embodiment, the bioprosthetic valve is positioned in the tubular leg portion and spaced proximal to the third stent a distance in the range from 0.0394 in. to 0.3937 in. (1.0 mm to 10.0 mm). In yet another embodiment as shown in FIG. 9, the bioprosthetic valve 246 is positioned in the tubular leg portion 224 and abuts 250 the third stent 246.

Figure 10:
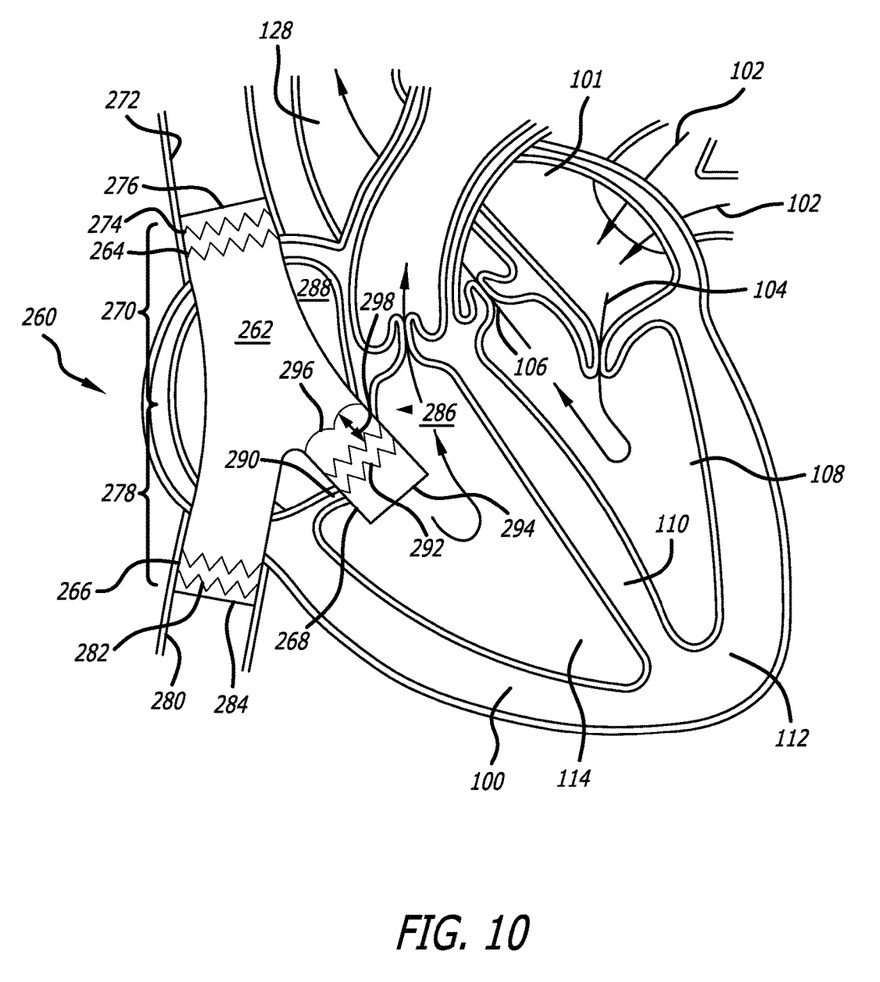
FIG. 10 schematically illustrates in cross-section the tubular endograft implanted in the SVC, IVC, and across the tricuspid valve.
Figure 11:
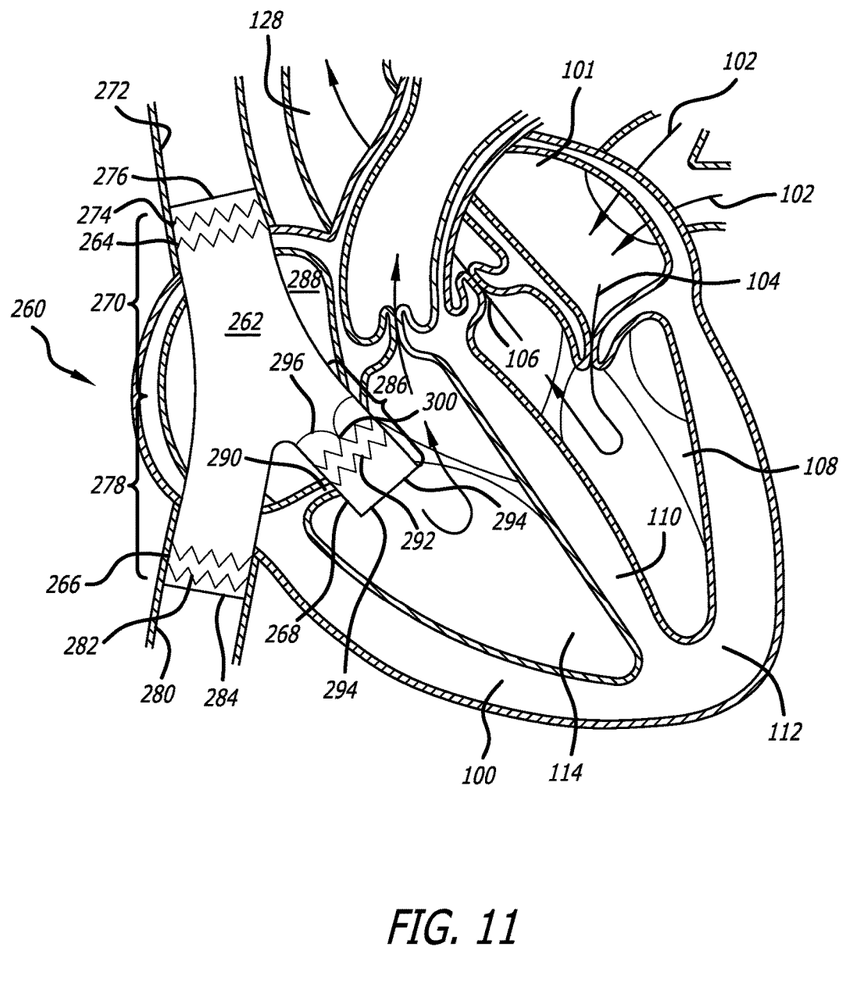
FIG. 11 schematically illustrates in cross-section the tubular endograft implanted in the SVC, IVC, and across the tricuspid valve, with the bioprosthetic valve abutting the third stent.

In another embodiment, a bifurcated endograft 260 has a Y-shaped configuration 262 and includes a first leg 264, a second leg 266, and a third leg 268, all in fluid communication with each other. The first leg has a first length 270 and is configured for extending into the SVC 272, and a first stent 274 adjacent a distal end 276 of the first leg for attaching the first leg to the SVC. The second leg 266 has a second length 278 and is configured for extending into the IVC 280, and a second stent 282 adjacent the distal end 284 of the second leg for attaching the second leg to the IVC. The third leg has a third length 286 and is configured for extending into the right atrium 288 and through the tricuspid valve 290. The third leg has a third stent 292 adjacent a distal end 294 of the third leg to hold open the tricuspid valve. A bioprosthetic valve 296 is positioned in the third leg 268 and spaced proximal to the third stent 292 a distance 298 in the range from 0.0394 in. to 1.1811 in. (1.0 mm to 30.0 mm). In another embodiment, the bioprosthetic valve is positioned in the third leg and spaced proximal to the third stent a distance in the range from 0.1969 in. to 0.7874 in. (5.0 mm to 20.0 mm). In another embodiment, the bioprosthetic valve is positioned in the third leg and spaced proximal to the third stent a distance in the range from 0.0394 in. to 0.3937 in. (1.0 mm to 10.0 mm). In yet another embodiment as shown in FIG. 11, the bioprosthetic valve 296 is positioned in the third leg 268 and is proximal to the stent and abuts 300 the stent.

The tubular graft 220 or tubular endograft 260 are formed from a flexible material such as PTFE, ePTFE, polyester, urethane, DACRON®, TEFLON®, or other distensible polymer material. The diameter of the tubular graft and tubular endograft as well as the length of the legs will vary depending on the size of the patient's heart, SVC, IVC and tricuspid valve.

The bioprosthetic valve 246, 296 disclosed herein is well known in the art. For example, a 23 mm Edwards Sapien valve (manufactured by Edwards Lifesciences, Irvine, Calif.) can be attached in the third leg 268 or tubular leg portion by using sutures or an adhesive. The valve can be collapsed during delivery and expanded in a known manner.

The first, second and third stents described herein are balloon expandable stents of the kind well known in the art. The stents plastically deform when expanded using a balloon in conjunction with a delivery catheter. One example of a balloon expandable stent is the VISION® stent manufactured by Abbott Cardiovascular Systems, Inc., Santa Clara, Calif. The VISION® stent is balloon expandable and made from a cobalt-chromium alloy to enhance visibility under fluoroscopy during stent delivery. The stents herein are attached to the tubular graft by known means, such as an adhesive. Upon expansion, the first, second and third stents form a seal with the SVC, IVC, and tricuspid valve, respectively.

The tubular graft 220 or bifurcated endograft 260 have a bifurcated or Y-shaped configuration as disclosed herein. The tubular graft and tubular endograft can be mounted on a bifurcated balloon delivery catheter system similar to that shown in U.S. Pat. No. 8,029,558, assigned to Abbott Cardiovascular Systems, Inc. The catheter shown in the '558 patent (FIGS. 28A-29) is designed to deliver a bifurcated stent in the coronary arteries, but it can be modified to carry and deliver the Y-shaped tubular graft 220 and tubular endograft 260 to the SVC, IVC and tricuspid valve. Thus, the present invention graft can be delivered percutaneously and implanted in the SVC, IVC and tricuspid valve using a modified version of bifurcated delivery catheter disclosed in the '558 patent.

In the preceding detailed description, reference to specific embodiments were described. It will, however, be evident that various modifications and changes may be made thereto without departing from the broader spirit and scope of the appended claims. The specification and drawings are, accordingly, to be regarded in an illustrative rather than a restrictive sense.

I claim:

1. A medical device for treating tricuspid valve regurgitation, comprising:
    a bifurcated endograft having a Y-shaped configuration including a first leg, a second leg and a third leg all in fluid communication;
    the first leg having a first length and being configured for extending into the superior vena cava (SVC) and a first stent adjacent a distal end of the first leg for attaching the first leg to the SVC;
    the second leg having a second length and being configured for extending into the inferior vena cava (IVC) and a second stent adjacent a distal end of the second leg for attaching the second leg to the IVC;
    the third leg having a third length and being configured for extending into the right atrium and through the tricuspid valve;
    the third leg having a third stent adjacent a distal end of the third leg to hold open the tricuspid valve; and
    a bioprosthetic valve positioned in the third leg and spaced proximal to the third stent a distance in the range from 0.0394 in. to 1.1811 in. (1.0 mm to 30.0 mm) wherein the bioprosthetic valve does not contact the third stent.

2. The medical device of claim 1, wherein the bioprosthetic valve is positioned in the third leg and spaced proximal to the third stent a distance in the range from 0.1969 in. to 0.7874 in. (5.0 mm to 20.0 mm).

3. The medical device of claim 1, wherein the bioprosthetic valve is positioned in the third leg and spaced proximal to the third stent a distance in the range from 0.0394 in. to 0.3937 in. (1.0 mm to 10.0 mm).

4. The medical device of claim 1, wherein the third stent has a non-collapsing lattice structure in order to hold open the tricuspid valve.

5. The medical device of claim 1, wherein the bifurcated endograft is formed from PTFE, ePTFE, polyester, urethane, polyethylene terephthalate, polytetrafluoroethylene, or other distensible polymeric material.

6. The medical device of claim 1, wherein the first stent, second stent and third stent are balloon expandable and plastically deform when expanded.

7. A medical device for treating tricuspid valve regurgitation, comprising:
    a tubular graft having a Y-shaped configuration including a tubular main body and a tubular leg portion extending from the tubular main body and being in fluid communication;
    the tubular main body having first end extending into the superior vena cava (SVC) and a first stent adjacent a first end for attaching the tubular main body to the SVC;
    the tubular main body having a second end extending into the inferior vena cava (IVC) and a second stent adjacent a second end for attaching the tubular main body to the IVC;
    the tubular leg portion being configured for extending into the right atrium and through the tricuspid valve;
    the tubular leg portion having a third stent adjacent a distal end of the tubular leg portion to hold open the tricuspid valve; and
    a bioprosthetic valve positioned in the tubular leg portion and spaced proximal to the third stent a distance in the range from 0.0394 in. to 1.1811 in. (1.0 mm to 30.0 mm) wherein the bioprosthetic valve does not contact the third stent.

8. The medical device of claim 7, wherein the bioprosthetic valve is positioned in the tubular leg portion and spaced proximal to the third stent a distance in the range from 0.1969 in. to 0.7874 in. (5.0 mm to 20.0 mm).

9. The medical device of claim 7, wherein the bioprosthetic valve is positioned in the tubular leg portion and spaced proximal to the third stent a distance in the range from 0.0394 in. to 0.3937 in. (1.0 mm to 10.0 mm).

10. The medical device of claim 7, wherein the third stent has a non-collapsing lattice structure in order to hold open the tricuspid valve.

11. The medical device of claim 7, wherein the bifurcated endograft is formed from PTFE, ePTFE, polyester, urethane, polyethylene terephthalate, polytetrafluoroethylene, or other distensible polymeric material.

12. The medical device of claim 7, wherein the first stent, second stent and third stent are balloon expandable and plastically deform when expanded.

13. A medical device for treating tricuspid valve regurgitation, comprising:
    a bifurcated endograft having a Y-shaped configuration including a first leg, a second leg and a third leg all in fluid communication;
    the first leg having a first length and being configured for extending into the superior vena cava (SVC) and a first stent adjacent a distal end of the first leg for attaching the first leg to the SVC;
    the second leg having a second length and being configured for extending into the inferior vena cava (IVC)

and a second stent adjacent a distal end of the second leg for attaching the second leg to the IVC;

the third leg having a third length and being configured for extending into the right atrium and through the tricuspid valve;

the third leg having a third stent adjacent a distal end of the third leg to hold open the tricuspid valve; and a bioprosthetic valve positioned in the third leg proximal to the third stent wherein the bioprosthetic valve abuts the third stent but does not extend into the third stent.

14. The medical device of claim 13, wherein the third stent has a non-collapsing lattice structure in order to hold open the tricuspid valve.

15. The medical device of claim 13, wherein the bifurcated endograft is formed from PTFE, ePTFE, polyester, urethane, polyethylene terephthalate, polytetrafluoroethylene, or other distensible polymeric material.

16. The medical device of claim 13, wherein the first stent, second stent and third stent are balloon expandable and plastically deform when expanded.

* * * * *